United States Patent [19]

Thoma et al.

[11] Patent Number: 5,408,381
[45] Date of Patent: Apr. 18, 1995

[54] CAPACITANCE HUMIDITY SENSOR

[75] Inventors: Paul E. Thoma, Cedarburg; Carl F. Klein, New Berlin; Alexander M. Blok, Bayside; Andrew R. Ralston, Madison, all of Wis.

[73] Assignee: Johnson Service Company, Milwaukee, Wis.

[21] Appl. No.: 234,221

[22] Filed: Apr. 28, 1994

[51] Int. Cl.$^6$ .............................................. H01G 7/00
[52] U.S. Cl. ................................. 361/286; 73/335.04; 29/25.42
[58] Field of Search ............... 361/286, 323; 24/25.42; 73/74, 335.04; 324/664

[56] References Cited

U.S. PATENT DOCUMENTS

| | | |
|---|---|---|
| 3,458,845 | 7/1969 | Thoma . |
| 3,582,728 | 6/1971 | Thoma . |
| 3,697,450 | 10/1972 | Takouaka et al. . |
| 3,802,268 | 4/1974 | Thoma . |
| 4,564,882 | 1/1986 | Baxter et al. . |
| 4,761,710 | 8/1988 | Chen ................. 361/286 |
| 4,865,698 | 10/1990 | Thoma et al. . |
| 5,050,434 | 9/1991 | Demisch ............. 361/286 |
| 5,072,262 | 12/1991 | Uekita et al. ....... 257/410 |
| 5,161,085 | 11/1992 | Sakai et al. .......... 361/286 |
| 5,177,662 | 1/1993 | Thoma . |

FOREIGN PATENT DOCUMENTS 62-316440 6/1989 Japan .
9103735 3/1991 WIPO .

OTHER PUBLICATIONS

IEE Transactions on Components, Hybrids, and Manufacturing Technology, vol. CHMT-2, No. 3, Sep. 1979 (pp. 321–323).

Johnson Controls, Inc. Bus/Tech Info Serv M47 "Advances in Polyimide Science and Technology" Oct. 30–Nov. 01, 1991 Ellenville, N.Y. pp. 618–635.

Primary Examiner—Bruce A. Reynolds
Assistant Examiner—Gregory L. Mills
Attorney, Agent, or Firm—Foley & Lardner

[57] ABSTRACT

A capacitance humidity sensor according to the invention has a film core which is in contact with a pair of conductive layers bonded to opposite faces of the core. The core is made of a polyimide having a dielectric constant which varies substantially linearly with humidity and which includes at least one ether linkage in the dianhydride portion thereof. The polyimide may also include at least one ether linkage in the diamine portion thereof and/or at least one fluorine atom in the diamine, dianhydride or both the diamine and dianhydride portions thereof.

6 Claims, 7 Drawing Sheets

CAPACITANCE HUMIDITY SENSOR

BACKGROUND OF THE INVENTION

1. Field of the Invention

The invention relates generally to capacitance humidity sensors, particularly to humidity sensors having a moisture sensitive dielectric layer interposed between a pair of conductors, and still more particularly to the use of a certain class of polyimide resins as the dielectric layer, i.e. those having at least one ether linkage in its dianhydride portion.

2. Description of the Prior Art

In commonly-owned U.S. Pat. No. 4,965,698 issued Oct. 23, 1990 to Thoma, et al. for "Capacitance Humidity Sensor", hereafter the '698 patent, a device of the general type with which the resin of the present invention is particularly well suited is described in considerable detail. The device of the '698 patent includes a core made of a material whose dielectric constant varies substantially linearly with humidity, such as a polyimide or polyparabanic acid material. The core is sandwiched between layers of polymeric material having conductive particles, such as conductive carbon particles, dispersed therein. In the '698 patent, the resin matrix for the conductive layers is described as containing certain crosslinked polymers formed by the reaction of a compound containing glucoside chains and a monomer or partial polymer capable of reacting with the hydroxyl groups of the glucosides. Specific examples of the disclosed materials included cellulose nitrate, cellulose triacetate, cellulose butyrate and, most preferably, cellulose acetate butyrate (CAB) crosslinked with urea formaldehyde or melamine formaldehyde.

Reference is made in the background section of the '698 patent to other types of known humidity sensors which include a dielectric layer and thin metal electrode conducting layers. Reference should be made to the patents cited in column 1 of the '698 patent for examples of such systems. The prior systems discussed in the earlier patent were deemed to have poor corrosion resistance, since thin metal electrodes can rapidly be destroyed by sulfur-based pollutants or chlorine.

Polyimides have been recognized as a particularly useful dielectric for humidity sensors because their dielectric constant is substantially linearly proportional to the moisture content. However, bonding between the polyimide and prior art metal foil or electrically conductive particle electrode layers was difficult without the use of adhesives because of the dissimilarity between the metal or electrically conductive particles and plastic. Examples of such prior art systems include U.S. Pat. Nos. 3,350,941 issued to Misevich in Nov., 1967; 4,429,343 issued to Freud on Jan. 31, 1984; 5,050,434 issued to Demisch on Sep. 24, 1991; and 5,069,069 issued to Miyagishi, et al on Dec. 3, 1991.

The '698 patent also discusses the use of mixtures of conductive particles, such as particles of silver or carbon black, dispersed in resins such as polyimides as shown, for example, in the Takenaka, U.S. Pat. No. 3,697,450 issued Oct. 10, 1972. It is also pointed out that other humidity sensors have employed various layers of crosslinked resins such as CAB crosslinked with urea formaldehyde. In one sensor, a crosslinked cellulose acetate butyrate core, containing conductive particles such as carbon, is sandwiched between a pair of outer resin layers free of carbon particles. See Thoma, U.S. Pat. No. 3,458,845 issued Jul. 29, 1969. In other humidity sensors, the outer resin layers contain the conductive particles and the inner resin layer does not; see Thoma, U.S. Pat. Nos. 3,582,728 issued Jun. 1, 1971; 3,802,268 issued Apr. 9, 1974; and *IEEE Transactions On Components, Hybrids and Manufacturing Technology*, Vol CHMT-2, No. 3, 1979, pgs. 321-323. Baxter, et al. U.S. Pat. No. 4,564,882 issued Jan. 14, 1986 describes a humidity sensing element wherein the dielectric layer can be made from either CAB or polyimide. Reference should also be made to the prior Thoma, et al. patent for discussions on the background use of polyparabanic acid polymers and on screen printing technologies.

In another commonly owned patent, U.S. Pat. No. 5,177,662 issued to Thoma on Jan. 5, 1993 for "Capacitance Humidity Sensor", the conductive layers utilize sulfur atoms in the backbone chain of the resin with conductive particles dispersed therein to improve corrosion resistance and performance.

The present invention addresses certain remaining drawbacks with such capacitance humidity sensors. Specifically, it is desirable to improve overall performance with a resin providing highly desirable humidity sensing characteristics and water vapor transmission rates and water absorption.

SUMMARY OF THE INVENTION

A capacitance humidity sensor according to the present invention has a dielectric core in contact with a pair of conductors. In its preferred aspect, the core is made of a material having a dielectric constant which varies substantially linearly with humidity and the conductive layers are made from a resin material having conductive particles dispersed therein. The preferred core resin is a polyimide which includes at least one ether linkage in its dianhydride portion, and which additionally may have at least one ether linkage in its diamine portion, and which also may have at least one fluorine atom in either or both of the dianhydride and diamine portions.

DETAILED DESCRIPTION OF THE PREFERRED EMBODIMENT

Figure 1:
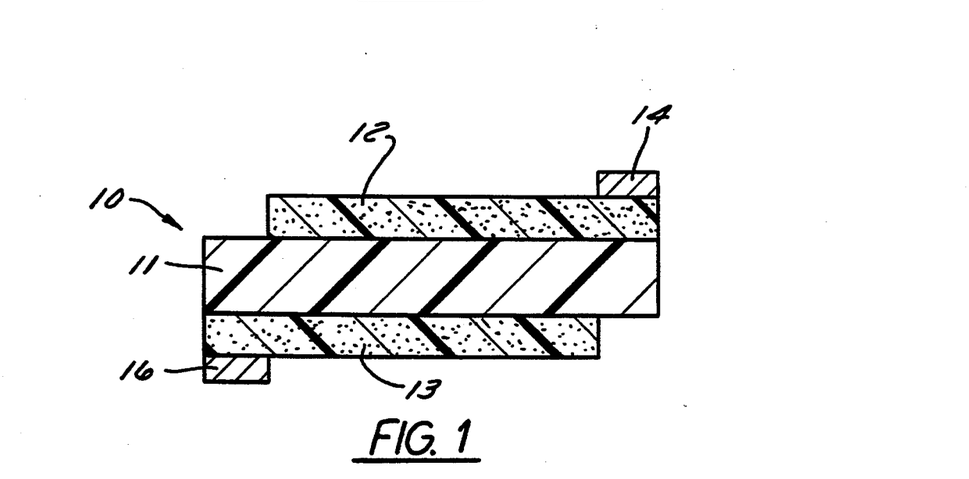
FIG. 1 is a cross-sectional view of a humidity sensing element according to one embodiment of the present invention.

The present invention provides a capacitance humidity sensor element in the form of a thin film. The system in which it is used will be illustrated by reference to one prior art sensor, but the new film may be used in any application where it is desired to sense humidity changes, as illustrated for example, in the above discussion of the prior art and in the systems described therein. Referring to FIG. 1, humidity sensor 10 according to the preferred embodiment of the invention includes a dielectric film 11 having a pair of electrically conductive layers 12, 13 on opposite sides thereof. Silver contacts 14, 16 on layers 12, 13 connect the sensor element to a source of electrical current. According to this invention, the specific resin used for the construction of film 11 is selected to give the sensor element 10 advantageous properties in a manner not achieved previously.

It is already known that dielectric film 11 should be a water absorbing material having a dielectric constant which changes predictably (preferably, essentially linearly) as a function of relative humidity. A specific class of polymers has been found to be especially useful as the dielectric layer of the humidity sensor of the invention. Each of the members of the class have backbone chains containing heterocyclic units in which one or more atoms in the heterocyclic unit is nitrogen, one or more carbon atoms in the heterocyclic unit has an oxygen atom double bonded to it (i.e., the unit contains one or more keto groups), and the heterocyclic unit is bonded into the polymer backbone through one or more nitrogen atoms of the heterocyclic ring. Suitable materials heretofore known for use as film 11 are described in detail in the aforementioned '698 patent, including structural formulations. They include the general class of polyimides and polyparabanic resins which have been found to be particularly useful because the hysteresis curves for such resins are substantially linear under a broad range of conditions. The resulting change in capacitance for a given change in humidity is quite constant over a temperature range of about 15° to 50° C., allowing the humidity sensor to be employed in harsh conditions.

The dielectric film 11 may be made as thin as possible for the desired capacitance and film strength, and, unlike many known sensors, can be thinner by half or more than the conductive layers. Film 11 can, for example, have a thickness of 0.005 inch or less, especially 0.0005 inch or less.

The resulting element 10 is extremely light and thin, and represents a departure from many prior sensors which employ a rigid base. According to the method of the invention described in the '698 patent, a film comprising the dielectric layer is made prior to the formation of the outer, integrally bonded conducting layers. Since the dielectric core is prepared as a separate film, its thickness, electrical properties and composition can be closely controlled.

Figure 2:
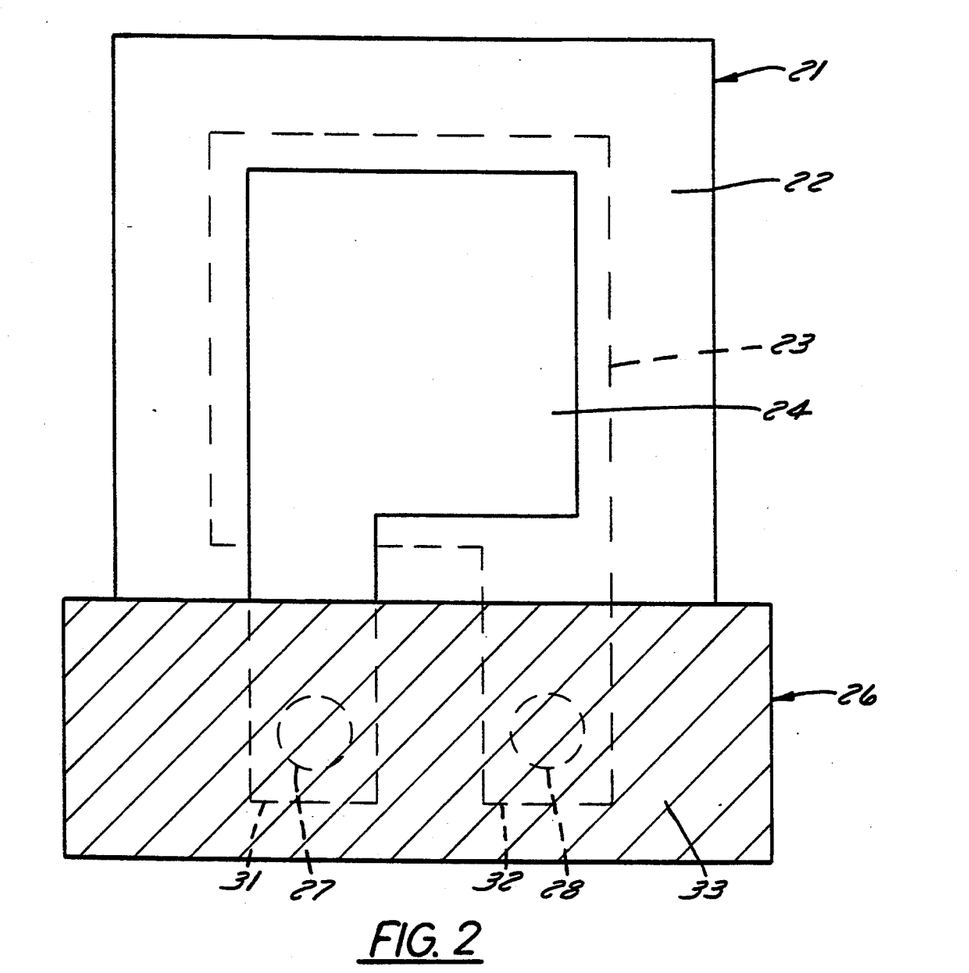
FIG. 2 is a top view of a humidity sensor shown in FIG. 1.

FIG. 2 illustrates a typical humidity sensor 21. Sensor 21 includes a dielectric film 22 made of a polymeric film such as the ones described above, a pair of conductive layers 23, 24 formed on opposite sides of film 22, and a holder 26. Outer conductive layers 23, 24 form the plates of the capacitor. Layers 23, 24 cover selected areas on opposite sides of dielectric film 22. The overlapping areas of the conductive layers 23, 24 comprise the active portion of the capacitance humidity sensor. Spots 27, 28 of conductive material, such as silver paint, are applied over conducting layers 23, 24 in areas where the layers 23, 24 do not overlap, for example in elongated tab portions 31, 32, which extend into holder 26. Electrical contact is made to spots 27, 28 by means of one or more conductive metal plates 33 forming part of holder 26 used to mount the humidity sensor.

Humidity sensor 21 may be used in combination with a variety of conventional circuitry to provide a humidity sensor, such as the ones described in Thoma, U.S. Pat. Nos. 3,582,728 and 3,802,268, as well as Carusillo, U.S. Pat. Nos. 4,558,274 and 4,661,768, the entire contents of which are hereby incorporated by reference. Such systems generally include the sensing element 21, a humidity indicator, such as a meter, a power source, and circuitry for interconnecting the above. The indicator provides a visual indication of changes in relative humidity as related to dielectric constant changes in the dielectric film.

The techniques for forming the preferred humidity sensor are also described in the aforementioned '698 Thoma, et al. patent, including the steps of forming the dielectric layer and the application of the conductive layers thereto. Generally, conductive layers 12, 13 and 23, 24 will be identical to one another, although for some applications, the thickness or electrical conductivity thereof may be varied. Screen printing is a particularly useful method for applying the compositions to the film, which can be held in place by suction applied through a fine screen holder positioned beneath the film. A stencil is placed over the film and the film is screen printed using conventional equipment, following which solvent is removed, thus resulting in a fusion of the conductive layers to the dielectric.

The conductive layers 12, 13, 23 and 24 of these preferred sensors employ conductive particles and should have a resistivity of about 50,000 $\Omega/\square$ or less, preferably 15,000 $\Omega/\square$ or less, as compared to dielectric film 11, which generally has a resistivity of at least about $10^{13}$ ohm-cm, preferably at least about $10^{15}$ ohm-cm at 25° C. and 50% relative humidity. Preferred conductive particles are those set forth in the aforementioned '698 and '662 Thoma patents, including carbon particles, particularly those which have long chains of particles to form agglomerates having an average agglomerate size of 10 microns, and preferably 0.25 micron or less. The conductive particles are generally used in an amount in the range of about 10–80 wt.%, the balance being the polymeric matrix to be described shortly. The conductivity of the particles can be enhanced by heating in vacuum, although heating in vacuum is not essential. Carbon particles, such as Vulcan ® XC-72 made by the Cabot Corporation, is one particularly preferred conductive material. It should be remembered throughout this discussion that the dielectric film 11 could be used with any of the other conductive layers of the prior art and that the conductive particle/resin layers are merely preferred.

The thickness of layers 12, 13 also influences the response time of the sensor, as does the molecular structure of the conductive layers, which is designed to have a high level of water transmission. The layers ideally should have a thickness of 0.01 inch or less, particularly 0.001 inch or less, to allow sufficiently rapid response time, e.g. 15 minutes or less.

The matrix for the conductive particles used in the preparation of conductive layers 12, 13 and 23, 24 are preferably selected from those resins described in the '698 and '662 Thoma patents. These polymers are moisture pervious, i.e., they transmit water molecules to the dielectric layer and they bond securely to the dielectric film.

To achieve integral bonding between the conductive layers and the dielectric core, physical and/or chemical bonds must exist between the layers. Sulfur containing polymers, such as polysulfone and polyethersulfones, are highly effective as the polymeric matrix for the conductive layer. These polymers have been found to have similar thermal and hygroscopic expansion coefficients as the heterocyclic polymers used in the dielectric layer and thus resist delamination during use due to changing temperature and relative humidities. Other sulfur containing polymers useful for the polymer matrix of the conductive layers include polyarylsulfones and polyphenylsulfones.

Sulfur containing polymers, such as polysulfone, can be bonded to a polyimide dielectric core by applying the polysulfone to the core layer as a solvent solution, and then heating the solution to a temperature at or above the glass transition temperature, Tg, of the polysulfone. A temperature of 190° C. to 325° C. for 30 minutes fuses polysulfone to the dielectric core to form a strong, adhesive bond between the conductive layer and the dielectric core.

In the present invention, the capacitance type humidity sensor is improved by using a specific class of polyimide as the dielectric film 11. The class of polyimides can be defined in most general terms as those having at least one ether linkage in the dianhydride portion of the polyimide. In addition, the polyimide may have one or more of the following:

at least one ether linkage in the diamine portion of the polyimide;

at least one fluorine atom in the dianhydride portion of the polyimide;

at least one fluorine atom in the diamine portion of the polyimide.

A preferred polyimide that is within the class described above is prepared from the dianhydride hydroquinone diether anhydride (available from Occidental Chemical Corporation, located at 2801 Long Road, Grand Island, N.Y. 14072)

and the diamine 2,2-Bis [4-(4-aminophenoxy) phenyl]-hexafluoropropane (available from Central Glass Company, Ltd. [address not known])

yielding a polyimide having a repeat unit structure shown below.

The polyimide is made by mixing the dianhydride and the diamine in equal molar amounts, in a solvent such as N,N-dimethylacetamide, to obtain a 17% solid content. The resulting solution is then cast on a glass plate and given an imidization cure for one (1) hour each at 100° C., 200° C. and 350° C. After cooling, the polyimide film is removed and processed into the capacitance humidity sensor.

Figure 3:
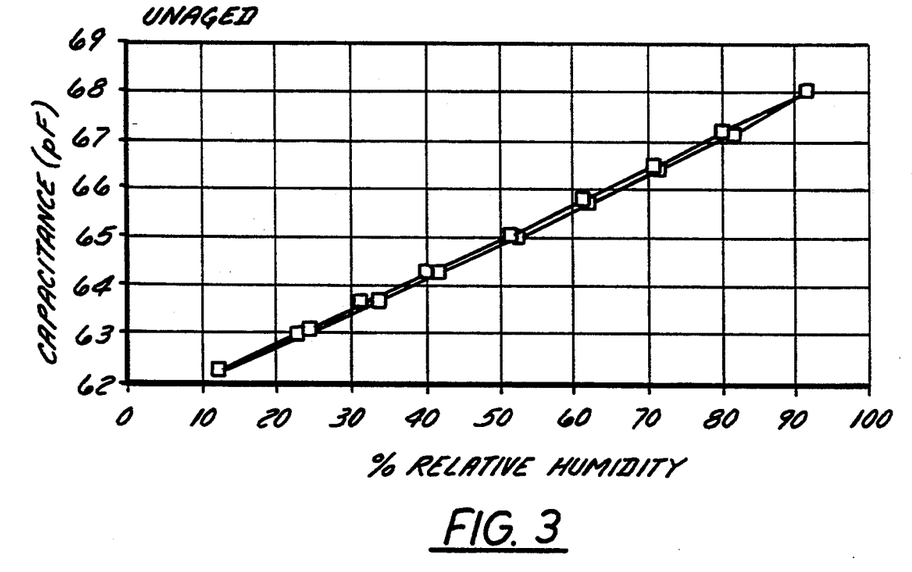
FIG. 3 is a humidity response curve for an unaged capacitor utilizing the resin of the preferred embodiment of the present invention.
Figure 4:
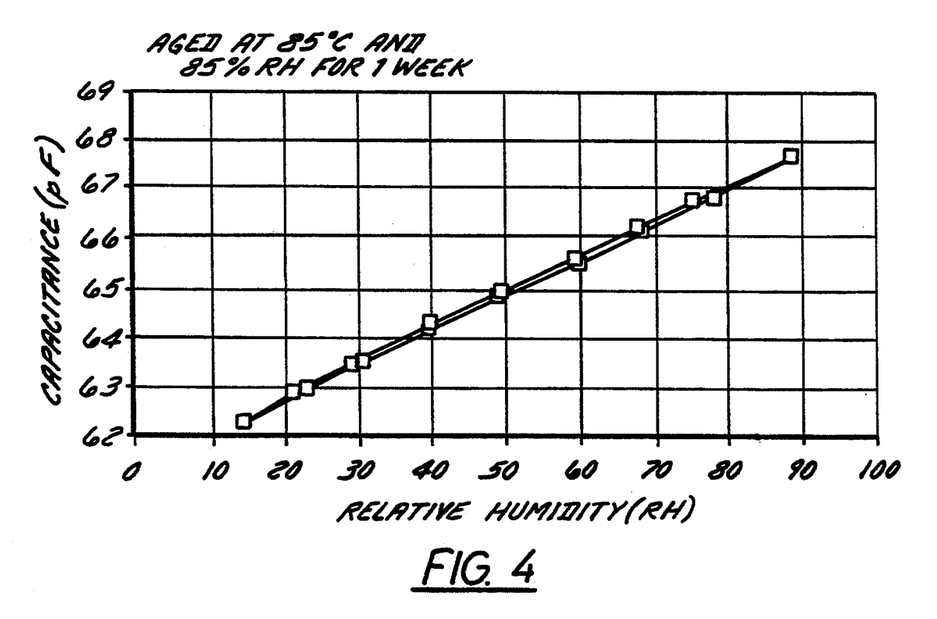
FIG. 4 is a humidity response curve for a capacitor according to the preferred embodiment of the present invention aged at 85° C. and 85% RH for one (1) week.
Figure 5:
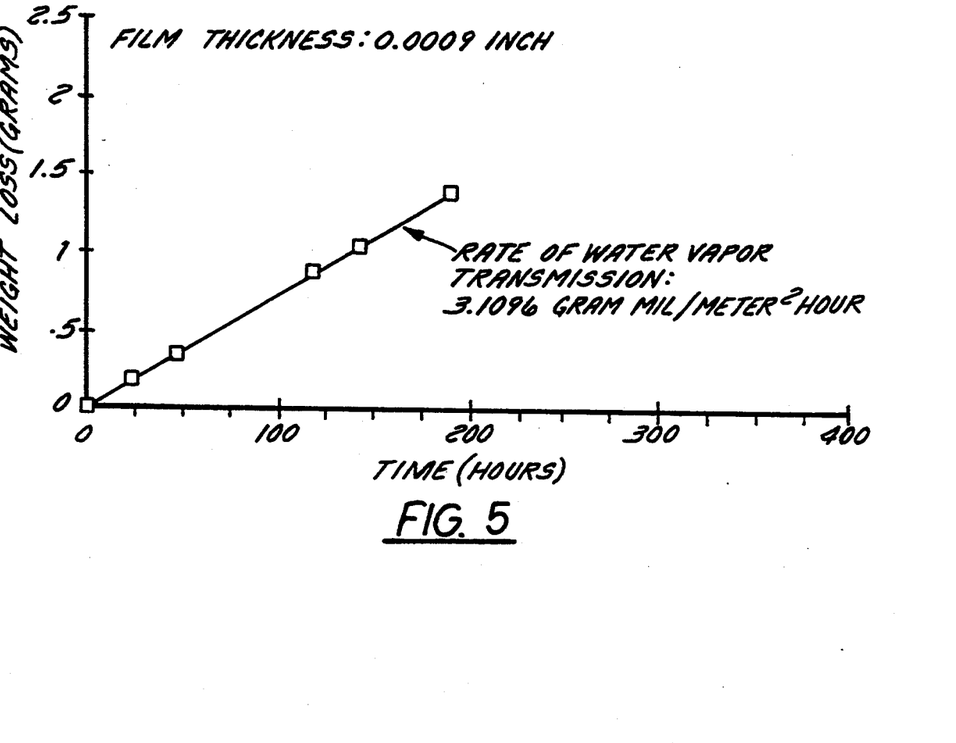
FIG. 5 is a water vapor transmission curve for a film of the resin of the present invention.
Figure 6:
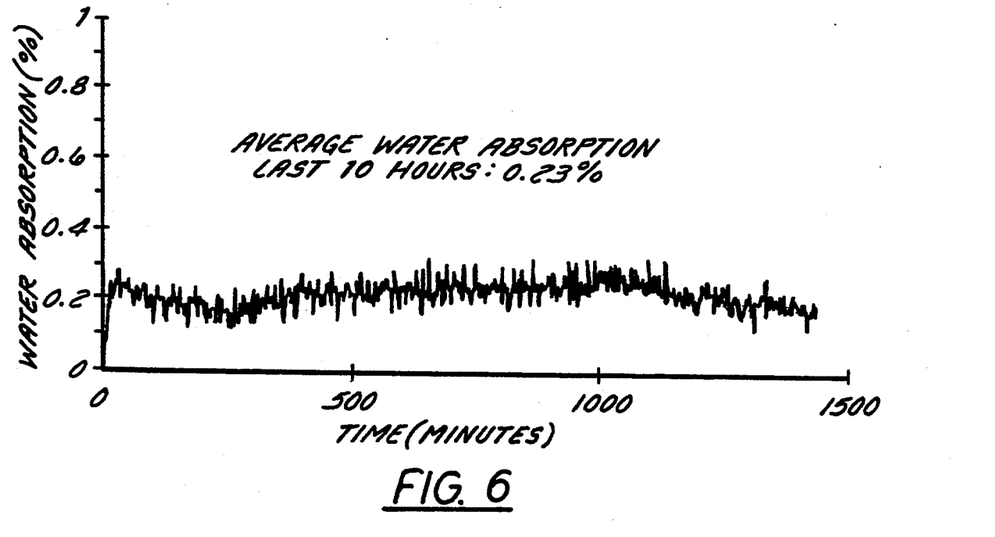
FIG. 6 is a water absorption graph at 50% relative humidity for the resin utilized in the present invention.

The capacitance humidity sensor using this dielectric polyimide has outstanding properties when compared to other capacitance humidity sensors. As shown in FIGS. 3 and 4, the humidity sensing characteristics are highly desirable in both the unaged condition and after aging at 85% RH and 85° C. for one (1) week. Water vapor transmission rates and the water absorption of this particular material are shown in FIGS. 5 and 6. In TABLE 1 below, comparative data is shown for a capacitance humidity sensor using the polyimide described above, as well as for sensors using DuPont's Kapton ® HN polyimide and Ube's Upilex ®R polyimide.

TABLE 1

| PROPERTY | HQDEA/4-BDAF | Kapton ® HN | Upilex ® R |
| --- | --- | --- | --- |
| Humidity Sensitivity picofarads/% RH for 100 pf Sensor | 0.11 | 0.21 | 0.12 |
| Sensor Hysteresis at 50% RH % RH | ≈1 | ≈4 | ≈2 |
| Deviation from Linearity at 50% RH % RH | 0 | ≈5 | ≈6 |
| Hydrolytic Instability at 50% RH % RH Shift | 0 | ≈10 | ≈4 |
| Water Absorption at 50% RH % Weight Gain | 0.23 | 1.2 | 0.7 |
| Rate of Water Vapor Transmission gram mil/meter² hour | 3.1 | 1.1 | 0.4 |

Although the humidity sensitivity of the capacitor made with the polyimide shown above is fairly close to the capacitor using the Upilex®R as the dielectric layer, the water absorption is ⅓ that of the Upilex®R material. The hydrolytic stability of the polyimide is attributed to the low water absorption of the polyimide. The relatively high humidity sensitivity of a capacitor made from this polyimide is attributed to differences in the humidity expansion coefficient of the various polyimides and/or differences in the effect water molecules have on the inherent permittivity (polarizability) of the polyimide molecules. The water vapor transmission rate of this polyimide is three times that of Kapton®HN and almost eight times that of the Upilex®R material.

Figure 7A:
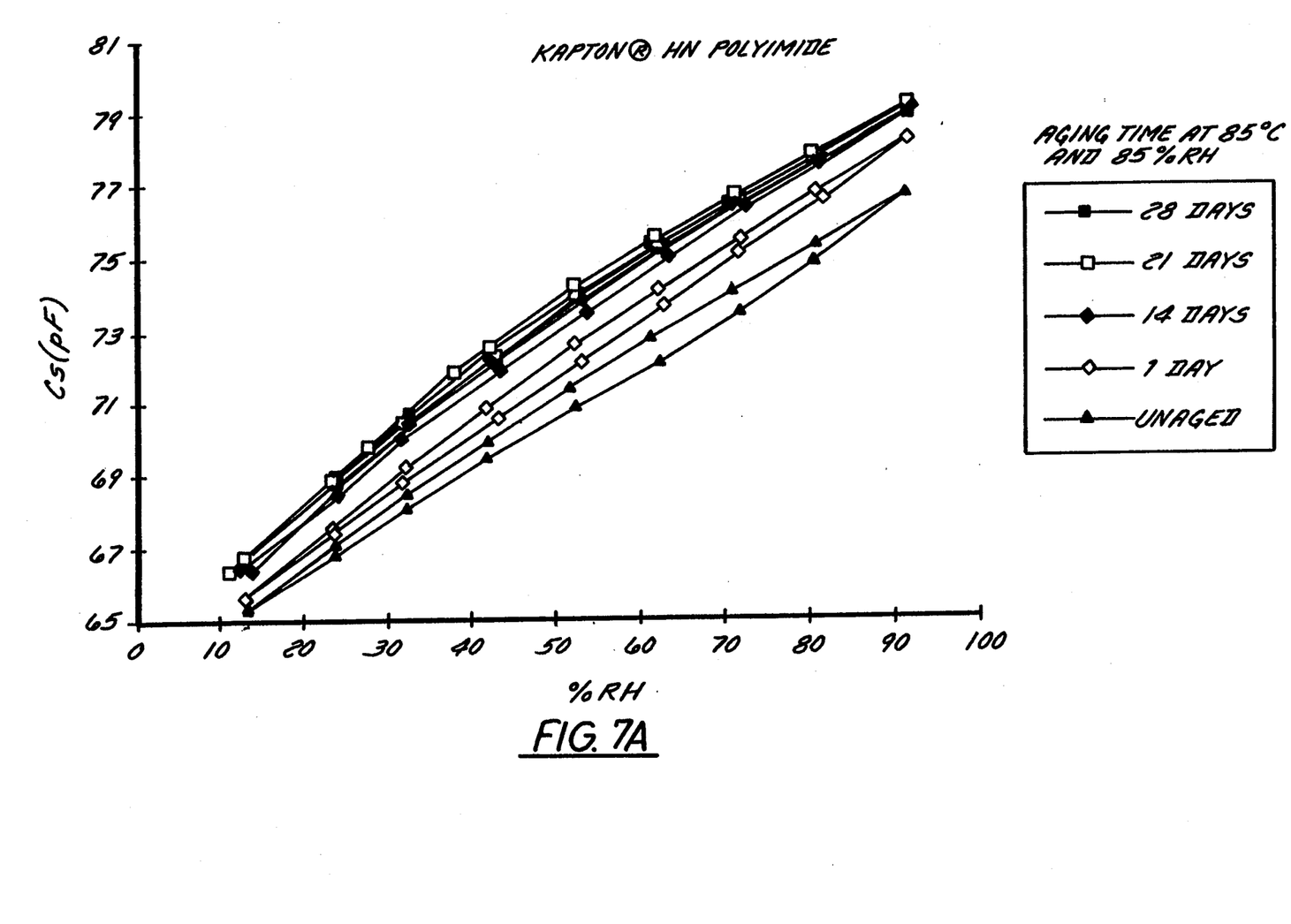
FIGS. 7A, 7B, and 7C are humidity response curves for Kapton ®HN polyimide, Upilex ®R polyimide and for the polyimide of the most preferred embodiment of the present invention showing data for unaged material and data for material aged at 1 day, 14 days, 21 days and 28 days.
Figure 7B:
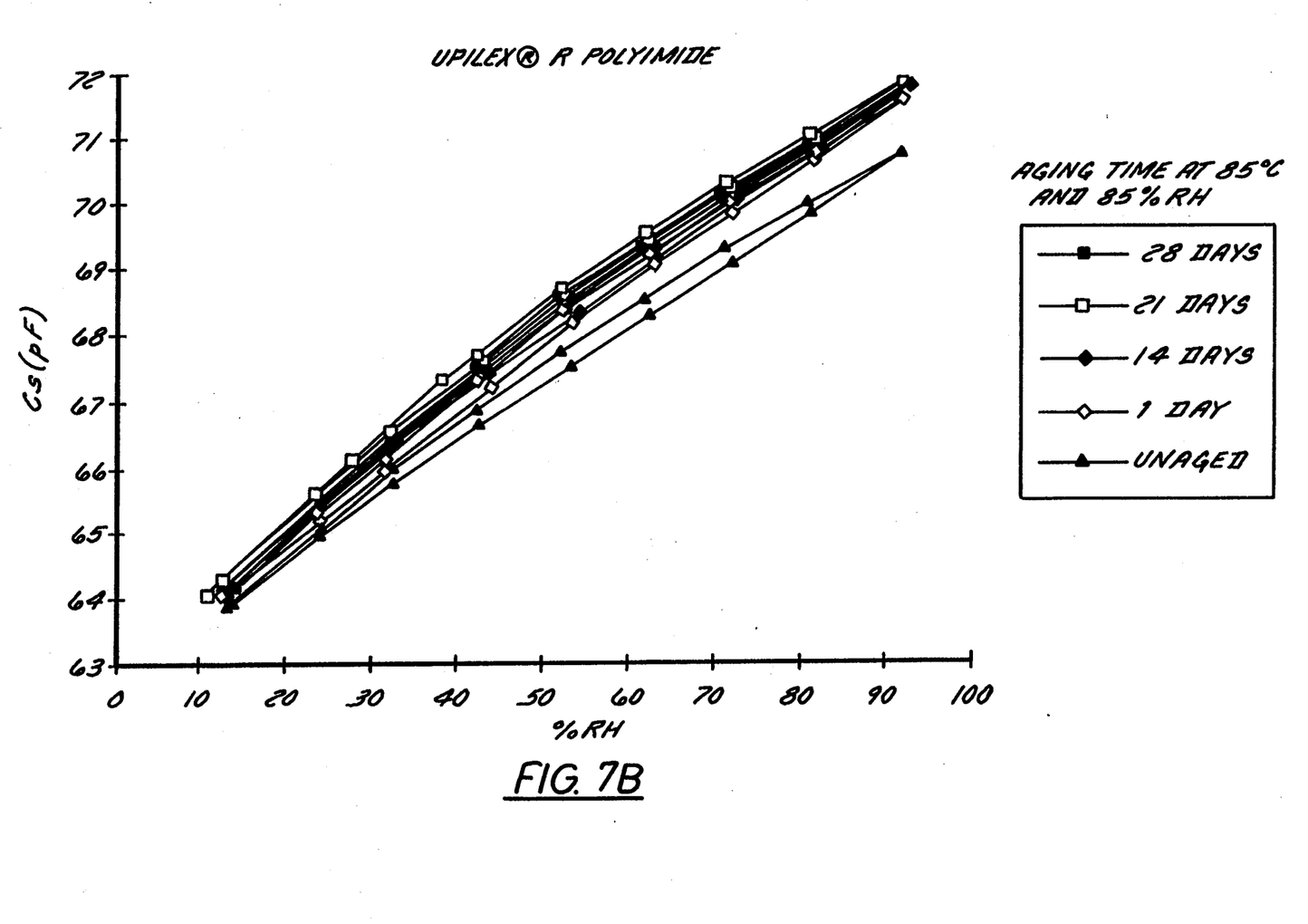
Figure 7C:
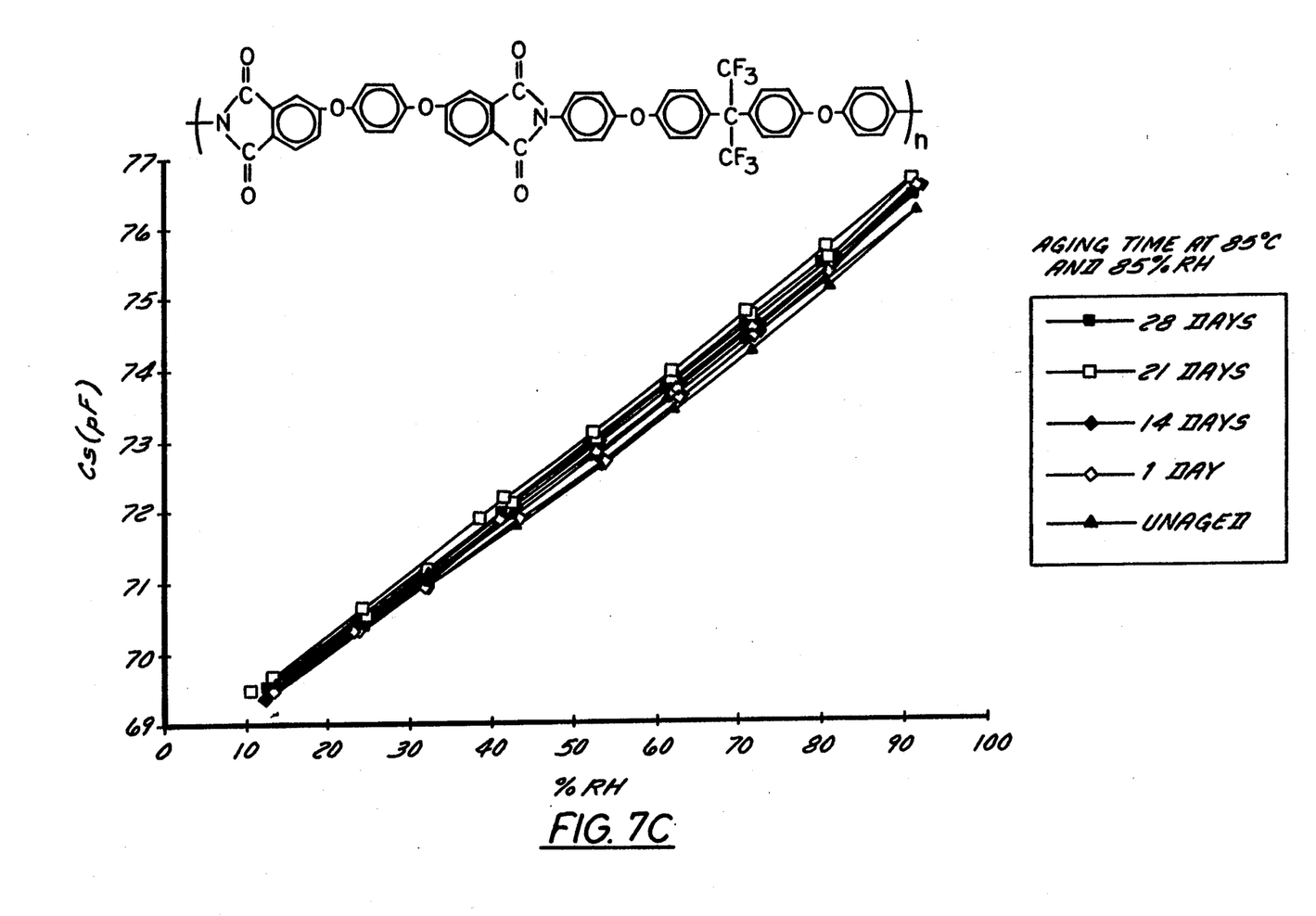

In addition to the advantageous properties already mentioned, the polyimide of the present invention has good sensitivity to relative humidity, fast response to changes in relative humidity, excellent hydrolytic stability, a near linear response to the relative humidity and small hysteresis. Perhaps this comparison is best demonstrated in FIGS. 7A–7C representing graphs of the capacitance vs. relative humidity for Kapton®HN polyimide, Upilex®R polyimide and the polyimide identified above with various aging times at 85° C. and 85% relative humidity. The near linearity and stability after aging is dramatically illustrated in these comparative FIGURES.

Another polyimide falling within the scope of the present invention is one having a repeat unit as follows:

made from a dianhydride 4,4'-oxydiphthalic anhydride:

(available from Occidental Chemical Corporation, located at 2801 Long Road, Grand Island, N.Y. 14072) and a diamine, namely 3,4'-oxydianiline:

(available from Kennedy and Klim, Inc., [address not known]).

Figure 8:
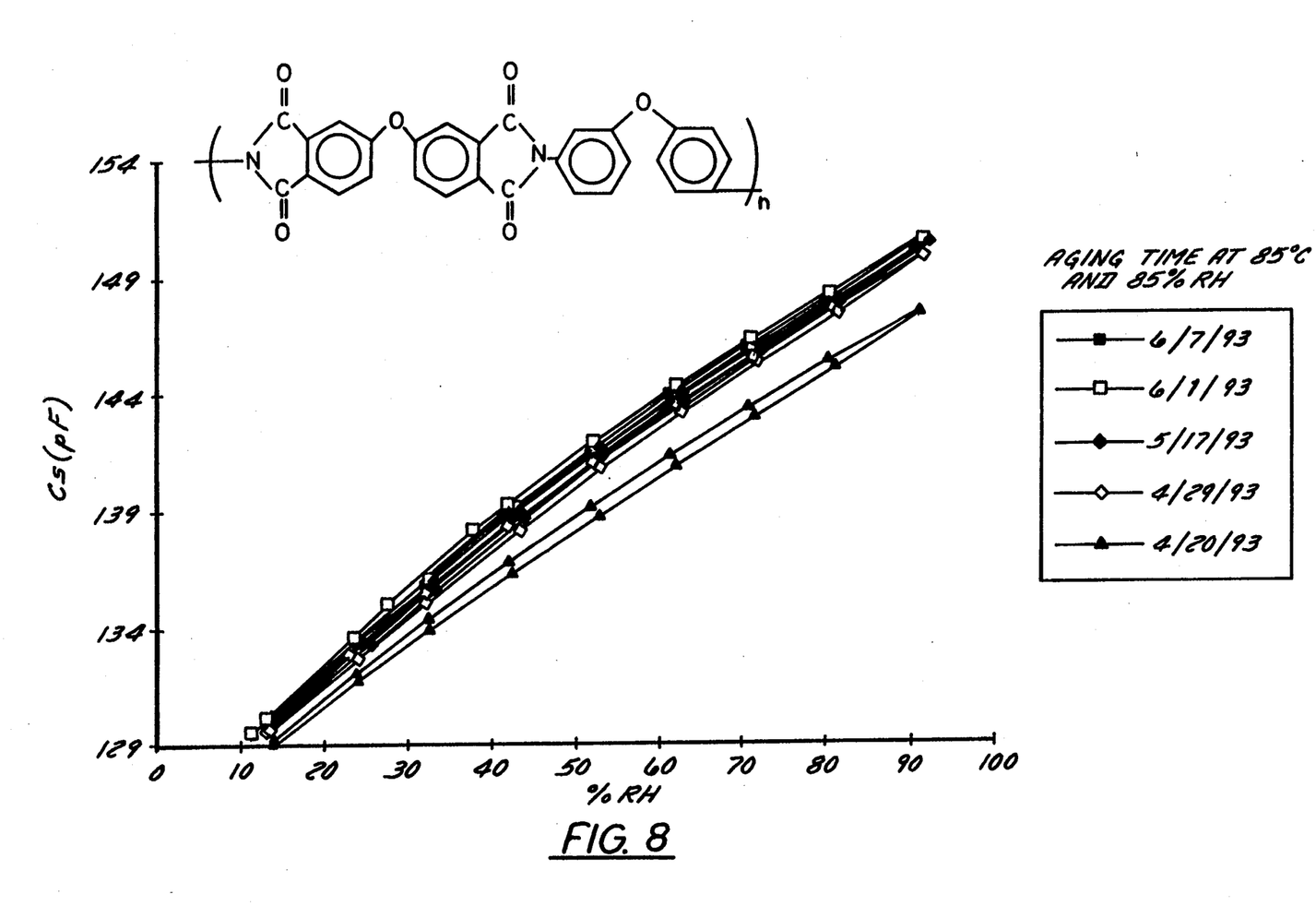
FIG. 8 is a humidity response curve for a polyimide of an alternate embodiment of the present invention showing aging data for the same periods shown in FIGS. 7A-7C.

The preparation of this material begins by subliming the dianhydride at 200° C.–210° C. and mixing it with the diamine in equal molar amounts in a solvent N,N-dimethylacetamide to obtain a 14% solid solution. The solution was cast onto a glass plate and given an imidization cure cycle at one (1) hour each at 100° C., 200° C. and 350° C., following which the film was removed from a glass plate. Its humidity response properties are illustrated in FIG. 8.

While the present invention has been described in connection with certain preferred formulations and materials, it is not to be limited thereby but is to be limited solely by the scope of the claims which follow.

What is claimed is:

1. A humidity sensor element comprising:
   a thin film consisting essentially of a dielectric, water-absorbing first polymer having a dielectric constant which varies substantially linearly as a function of relative humidity, the first polymer being a polyimide made from a dianhydride and a diamine each containing at least one ether linkage and at least one fluorine atom being present in the dianhydride or the diamine or in both the dianhydride and the diamine; and
   a pair of thin, electrically conductive layers disposed on opposite sides of said film and integrally bonded thereto.

2. The element of claim 1 wherein the film has a thickness of 0.01 inch or less.

3. The element of claim 1 wherein the repeat unit structure for the first polymer is the following:

4. A method for making a humidity sensor element, comprising:
   (a) the step of disposing a piece of a thin film made of a dielectric, water absorbing first polymer having a dielectric constant which varies as a function of relative humidity on a holder, the first polymer being a polyimide made from a dianhydride and a diamine, each containing at least one ether linkage and at least one fluorine atom being present in the dianhydride or the diamine or in both the dianhydride and the diamine;

(b) the step of applying a stencil over the film;

(c) screen printing the film through the stencil with a liquid conductive composition to form a first conductive layer on one side of the film; and (d) repeating steps b–c to form a second conductive layer on the side of the film opposite the first conductive layer.

5. The method of claim 4 wherein the film has a thickness of 0.01 inch or less.

6. The method of claim 4 wherein the repeat unit structure for the first polymer is the following:

* * * * *